(12) United States Patent
Caceres et al.

(10) Patent No.: US 7,794,485 B2
(45) Date of Patent: Sep. 14, 2010

(54) COMPRESS WITH COOLING EFFECT IN STERILE PACK

(76) Inventors: Patrick Caceres, 13bis Chemin des Balmes, F-69110 Sainte Foy-les-Lyon (FR); Franck Caceres, 6 Rue de L'Abandance, F-69003 Lyon (FR)

(*) Notice: Subject to any disclaimer, the term of this patent is extended or adjusted under 35 U.S.C. 154(b) by 1053 days.

(21) Appl. No.: 11/155,550

(22) Filed: Jun. 20, 2005

(65) Prior Publication Data
US 2005/0283212 A1 Dec. 22, 2005

(30) Foreign Application Priority Data
Jun. 18, 2004 (FR) .................. 04 06633

(51) Int. Cl.
*A61F 7/00* (2006.01)
*A61F 7/10* (2006.01)
(52) U.S. Cl. ........................ 607/114; 607/96
(58) Field of Classification Search ............... 607/114
See application file for complete search history.

(56) References Cited

U.S. PATENT DOCUMENTS

| | | | | |
|---|---|---|---|---|
| 3,455,438 A | * | 7/1969 | Fitzgerald | 206/440 |
| 3,874,504 A | * | 4/1975 | Verakas | 206/219 |
| 3,893,834 A | | 7/1975 | Armstrong | |
| 4,252,119 A | * | 2/1981 | Coates | 604/306 |
| 4,474,016 A | * | 10/1984 | Winchell | 435/284.1 |
| 5,300,105 A | * | 4/1994 | Owens | 607/114 |
| 5,447,532 A | | 9/1995 | Furuya | |
| 5,534,020 A | * | 7/1996 | Cheney et al. | 607/108 |
| 5,597,577 A | * | 1/1997 | Mathewson | 424/402 |
| 5,681,579 A | * | 10/1997 | Freeman | 424/448 |
| 5,709,089 A | * | 1/1998 | Dawson et al. | 62/4 |
| 5,800,483 A | | 9/1998 | Vought | |
| 6,524,331 B1 | | 2/2003 | Kohout et al. | |
| 2004/0024438 A1 | | 2/2004 | von Hoffmann et al. | |

FOREIGN PATENT DOCUMENTS

WO   WO 03/055425 A1   7/2003

* cited by examiner

*Primary Examiner*—Roy D Gibson
*Assistant Examiner*—Kaitlyn E Helling
(74) *Attorney, Agent, or Firm*—Oliff & Berridge, PLC

(57) ABSTRACT

The invention relates to a compress with a cooling effect, based on particles (6) of a polymer that has a high water absorption capacity, which comes enclosed with a reserve of water to activate it in an item (2) which comprises, inside a watertight outer sachet (3), on the one hand an inner pouch (4) filled with water and sealed in a watertight manner by a wall comprising a frangible region (10) and, on the other hand, the compress (1) produced in the form of a wrapper (5) at least partially permeable to water and containing the polymer particles (6) in the dry state. The sachet (3) is made of a material of a nature able to keep the pouch (4) and the compress (1) sterile.

20 Claims, 2 Drawing Sheets

_US 7,794,485 B2_

COMPRESS WITH COOLING EFFECT IN STERILE PACK

BACKGROUND OF THE INVENTION

The present invention relates to the design and production of a compress in a sterile pack which, after activation, has a cooling effect.

A compress is to be understood as meaning any type of dressing, bandage or similar item intended to be applied to the body for a medical treatment or other operation.

The compress according to the invention is intended to be used for cryothermic care. It has long been known that cold is very effective in treating certain physical afflictions and, in particular, in relieving pain or in reducing swelling. In certain cases, it is necessary for the cold to be applied to the part of the body that requires treatment while at the same time respecting conditions of sterility. This is particularly true in the case of wounds or areas where the skin is irritated, which may become infected upon contact with microbial agents. When treating such wounds, it is absolutely essential that anything placed in contact with the wound be sterile.

The compress according to the invention can be used in any place where it may be desirable to deliver cold to the body, whether this be a human body or the body of an animal, under sterile conditions. It is particularly advantageous in a hospital environment because, in such an environment, it is de rigueur to use only sterile equipment in order to minimize the spread of infections, especially nosocomial infections.

Compresses with a cooling effect intended to be applied to the body are known from the prior art. Such compresses, which are entirely advantageous from the point of view of the effectiveness of the cold delivered and their comfort of use have been designed in particular on the basis of polymers with a high water absorption capacity, which produce cold by evaporation and desorption of the absorbed water. By way of example, mention may be made of the compresses described in document U.S. Pat. No. 5,597,577. These compresses are made up of particles of absorbent polymer contained within a textile wrapper. In order to exert their cooling action, they need first of all to be activated, that is to say immersed in water, so that the polymer particles swell by absorbing water. They then exert their cooling effect, by evaporation and desorption of the water absorbed by the polymer. Such compresses are entirely suited to day-to-day use by private individuals, in order to relieve the pain caused, for example, by a muscle or ligament injury or even a migraine. However, they are not suitable for use in a hospital environment for example, because they do not come in sterile form, and it is furthermore impossible to activate them under satisfactory conditions of sterility.

Document U.S. Pat. No. 5,447,532 proposes, in order to activate a cooling compress based on an absorbent polymer, for it to be placed inside a plastic bag, and then for the water required to activate it to be poured into this bag. The bag is then closed up for the time needed for the compress to absorb the water. This method of activation does not allow a sterile compress to be contained. The problem of the sterility of the compress is not tackled in that document.

SUMMARY OF THE INVENTION

The invention aims to remedy these disadvantages by proposing a system for preparing a compress based on absorbent polymer which preserves the sterility of the elements of which it is composed. This compress may thus be used in complete safety, particularly in a hospital environment. Applied to the part of the body that is to be relieved, it delivers cold to that site for a relatively long period of time.

The cooling compress chosen within the context of the invention is based on particles of a polymer with a high water absorption capacity. Compresses of this type, which are known from the prior art, have good inertia in respect of their regaining of temperature, and therefore deliver cold very effectively. Their principle of operation is well known from the prior art. In particular, for that, reference may be made to the aforementioned document U.S. Pat. No. 5,597,577.

The compress according to the invention comes enclosed with a reserve of water to activate it in an item which comprises, inside a watertight outer sachet, the following two elements: on the one hand an inner pouch filled with water and sealed in a watertight manner by a wall comprising a frangible region and, on the other hand, the compress produced in the form of a wrapper at least partially permeable to water and containing the polymer particles in the dry state. The sachet is made of a material of a nature able to keep the pouch and the compress sterile. It is sealed watertight and impervious to germs. The pouch containing the water and the various elements that make up the compress are made of materials which are compatible with a sterilization treatment.

The wrapper of the compress which contains the particles of water-absorbing polymer is advantageously designed such that when the particles are in the dry state, a sufficient volume remains inside the wrapper to allow the particles to swell by absorbing water. Thus, when the particles are in the dry state, the compress is in flattened form, the opposite walls of the wrapper being collapsed against one another. By contrast, when the particles contained in the wrapper absorb water, they expand under the effect of this absorption, and the compress then takes on a swollen state, with a thickness of the order of 1 centimeter. When the compress is applied to the body of an individual, the water contained in the particles heats up and vaporizes. It is then desorbed from the particles, at the same time creating a cooling effect.

The various constituents of the item according to the invention are chosen to be compatible with a sterilization treatment. According to a preferred embodiment of the invention, the outer sachet, the inner pouch and the compress have, in particular, the special feature of being compatible with a sterilization treatment using gamma-radiation, particularly at 20 to 50 kGy, and/or with a sterilization treatment using beta-radiation.

It is thus advantageously ensured that the item according to the invention, that is to say the outer sachet containing the compress and the water-filled pouch can be subjected to a sterilization treatment. In addition, the material of which the walls of the outer sachet are made is of a nature able to keep the pouch and the compress sterile. This material in particular forms an anti-germ barrier which prevents any contamination external to the sachet from entering the latter. Thus, once the sterilization treatment has been carried out, the item according to the invention can be kept in complete safety: the elements it contains, particularly the compress and the pouch of water, are kept sterile therein.

In order to be able to use the compress for its cooling effect, it needs to be activated. In principle, as was explained hereinabove in this description, this is performed by immersing the compress in water so that the polymer particles swell by absorbing water, then by placing the compress in the freezer for a few hours. The purpose of this last step is to lower the temperature of the water contained in the particles and cause it to pass to the solid state. Thus, when the compress is subsequently applied to the body, the water, before vaporizing, has first of all to liquefy. This results in greater inertia in terms of the regaining of temperature by the compress.

With the item according to the invention, and in this the present invention proves to be entirely advantageous, the activation of the compress is performed under sterile conditions, and very simply. Pressure is exerted, through the outer sachet, on the inner pouch, so as to break the frangible region thereof. The item according to the invention is advantageously designed in such a way that, during this operation, there is no risk that the outer sachet will yield and open up under the effect of this pressure. Thus, according to an advantageous feature of the invention, the outer sachet is closed in a strong fashion and in such a way that, in order to open it, far more pressure that the pressure needed to break the frangible region of the inner pouch would have to be exerted.

The water is released from the inner pouch; it spreads out in the sachet; it comes into contact with the compress; it crosses the water-permeable wrapper and it is absorbed, and retained, by the polymer particles. Once the compress has swelled with water, the item in its entirety can be placed somewhere cold, particularly in the freezer, for long enough to allow the water to cool. Throughout all these steps, the outer sachet is never opened which means that the compress, and the water it absorbs, are constantly in a sterile environment.

Finally, at the moment desired for use, the outer sachet is opened, preferably observing optimum sanitary conditions (wearing gloves and using sterile tweezers or tongs for example), and the compress is extracted therefrom. It then provides an effective cooling effect.

According to an advantageous feature of the invention, the inner pouch contains a volume of water more or less equal to, and preferably slightly less than, the volume available in the wrapper so as to allow the particles to swell by absorbing water. When evaluating this volume, the inherent ability of the walls of the wrapper to expand as the swollen polymer particles exert pressure on them is not taken into consideration as this expansion capability is negligible.

This feature is particularly advantageous in that it makes it possible to ensure that a sufficient amount of water will be present in the item to allow the wrapper to be filled completely. The compress will thus generate cold to the maximum of its capacity, since it is the amount of water absorbed by the particles which is at the root of the cooling effect: the more water the particles have absorbed, within the limits, of course, of their intrinsic absorption capacity, the longer and more durable will be the cold effect produced by the compress.

In addition, by also ensuring that the amount of polymer particles present in the wrapper will be sufficient to absorb all the water contained in the pouch, the fact of introducing into this pouch an amount of water just equal to, or even very slightly less than, the volume remaining available in the wrapper of the compress, guarantees that all the water released form the inner pouch will enter and be retained in the wrapper. Thus, no volume of free water will remain inside the sachet. This is particularly advantageous because water that remains free in the sachet could, during the time that the item spends in the freezer, freeze on the outer surface of the compress, and adhere to the latter. This would then result in a certain impediment for the end-user of the compress.

According to some embodiments which are preferred in industrial practice, the invention satisfies the following characteristics, implemented separately or in each of their technically feasible combinations.

These characteristics take account of the fact that the compress, which is intended to be applied to the skin, and even to sensitive areas, such as wounds, has to meet safety conditions in respect of the user. Thus, all its constituent parts, particularly the polymer particles, are nontoxic to the organism.

In addition, the characteristics of the item according to the invention in particular allow additional objectives of the invention to be satisfied, these being to ensure good effectiveness of the cold delivered and good comfort of use of the compress once activated.

In some preferred embodiments of the invention, the polymer particles are present in the wrapper in an excess of 400 to 800%, and preferably of about 600%, by comparison with the quantity that would be just enough to fill the wrapper when the particles have swelled fully by absorbing water.

A markedly greater amount of absorbent polymer particles than the amount that would normally be required for the compress to produce its full cooling effect is thus placed in the wrapper. This characteristic advantageously guarantees that even if, during a sterilization treatment, some of the particles become degraded, the wrapper will still contain working particles, that is to say ones able to absorb a large amount of water and retain it, releasing it only in the vapor state, so as the compress delivers intense cold for a lasting period of time.

In preferred embodiments of the invention, the polymer particles used have a water absorption capacity of about 60 times their volume. For a wrapper with an internal volume of 100 ml, the amount of polymer particles in the dry state contained in the wrapper is between 6 and 13 ml, preferably about 10 ml. The associated inner pouch contains a volume of water equal to the complement of this volume of particles needed to make up to 99 ml. Thus it is advantageously guaranteed that there will still be enough working polymer particles after the sterilization treatment for the compress to achieve an effective cooling effect. In addition, the four parameters that are: the internal volume of the wrapper, the absorption capacity of the polymer particles and the quantity thereof in the dry state present in the wrapper, providing a significant excess in order to alleviate the problem of partial degradation of the particles during the sterilization, and finally the associated volume of water inside the outer sachet, are advantageously chosen, in conjunction with one another, in such a way as to give the compress the maximum cooling capacity at the same time as good comfort of use.

In preferred embodiments of the invention, the polymer is a crosslinked sodium polyacrylate. Such a polymer is nontoxic to the organism.

According to an advantageous feature of the invention, the wrapper is made of a water-permeable nonwoven strong enough not to yield under the effect of the forces exerted on it by the polymer particles expanding under the effect of the absorption of water. It is also advantageous within the context of the invention to envisage for the material of which the wrapper is made to allow water to pass, but not to retain it. Thus, the walls of the wrapper, and therefore the exterior surface of the compress which is intended to come into contact with the body remain dry. This results in better comfort for the user because the feeling felt on the skin when the compress is applied thereto is that of dry coldness.

With the same goal of ensuring that the compress is very comfortable to use, in preferred embodiments of the invention, the outer sachet is airtight and the pouch of water and the compress are vacuum packed therein.

To this end, the outer sachet is made of an airtight material. Any material exhibiting this property may be used in the context of the invention, with the essential proviso that is should also constitute a barrier against germs. For practical reasons, it is preferable to use an outer sachet made of a plastic which is such that it is impervious to germs, to air and, of course, to water so as to avoid risks of leakage. Furthermore, the outer sachet is sealed against the three elements that are: water, germs and air, particularly by continuous weld lines.

Vacuum packing advantageously avoids a layer of ice forming on the exterior surface of the compress during the time that the latter spends in the freezer. What happens is that air present inside the sachet always contains traces of moisture. If a large amount of air is allowed to remain with the sachet, when the item is placed in the freezer, this moisture condenses on the surface of the compress and, as it cools, forms a layer of ice thereon. This layer of ice is a source of inconvenience to the user of the compress.

By contrast, applying a reduced pressure inside the sachet eliminates most of the moisture therein, and this then prevents the layer of ice from forming. In practice, a pressure corresponding to about 95% air vacuum, applied by means of conventional evacuating apparatus, is sufficient for this purpose.

In addition, the fact of placing the interior of the sachet under reduced pressure offers other advantages, due to the fact that, under these circumstances, the walls of the outer sachet are pressed against the respective surfaces of the pouch of water and of the compress.

On the one hand, this then reduces the risk of the outer sachet opening when pressure is applied to the item in order to rupture the frangible region of the inner pouch. In effect, when reduced pressure is applied to the inside of the sachet, the walls thereof are pressed firmly against the pouch of water: the forces exerted on the walls of the sachet are therefore transmitted directly to those of the pouch. The latter is therefore encouraged to rupture.

On the other hand, when the polymer particles swell, and the compress increases in thickness, the walls of the outer sachet pressed against the walls of the wrapper reinforce the latter walls, making them better able to withstand the forces exerted on them by the particles.

Finally, the application of reduced pressure also has the effect of pressing the pouch of water against the surface of the compress, and therefore encouraging the water released from the pouch to penetrated the compress directly.

The wrapper of the compress according to the invention may have various shapes and various sizes. Thus, a whole range of compresses may be formed, each tailored to a particular application.

In some preferred embodiments of the invention, the opposite faces of the wrapper of the compress are connected together along various longitudinal lines so as to form a plurality of elongate compartments in which the polymer particles are uniformly distributed. This embodiment advantageously allows the compress to have a large area of contact with the skin so that the cold can be applied uniformly to the entire region of skin to which the compress is applied.

According to an advantageous secondary feature of the invention, the longitudinal lines are produced by ultrasonic welding in continuous lines or criss-cross lines. This advantageously makes it possible to obtain tightness against the passing of polymer particles from one compartment to the other. The weld lines obtained are also mechanically able to resist the tensile forces exerted on them by the polymer particles swelling as they absorb water.

The invention also related to a method of manufacturing the item so that a compress based on polymer particles with a high water absorption capacity can be offered in sterile form.

This method is characterized by the following steps.

A compress in the form of a wrapper containing the polymer particles is prepared first of all.

Then the compress and the inner pouch filled with water are introduced into the outer sachet.

A reduced pressure is applied to the inside of the sachet and the sachet is sealed in a tight manner.

Finally, the entity is sterilized by treating it with gamma-radiation, at 20 to 50 kGy. Sterilization may also, in preferred embodiments of the invention, be performed with beta-radiation.

According to the invention, the compress is then activated and used as follows.

Without opening the outer sachet, pressure is exerted on the inner pouch in order to break its frangible region. The water thus released from the inner pouch is allowed to penetrate the compress.

The item is then optionally placed somewhere cold, particularly in a freezer, for a time of between 15 and 90 minutes for example. This step makes it possible to increase the cooling capacity of the compress.

Finally, the outer sachet is opened at the time of use in order to remove the sterile cooling compress therefrom.

The compress can then be applied to the desired part of the body, in complete safety, because is meets the required conditions of sterility.

The compress according to the invention is particularly suited to single use.

BRIEF DESCRIPTION OF THE DRAWINGS

The invention will be described more fully now in the context of some preferred characteristics and their advantages, with references to FIGS. 1 to 4, in which.

DETAILED DESCRIPTION OF THE INVENTION

Figure 1:
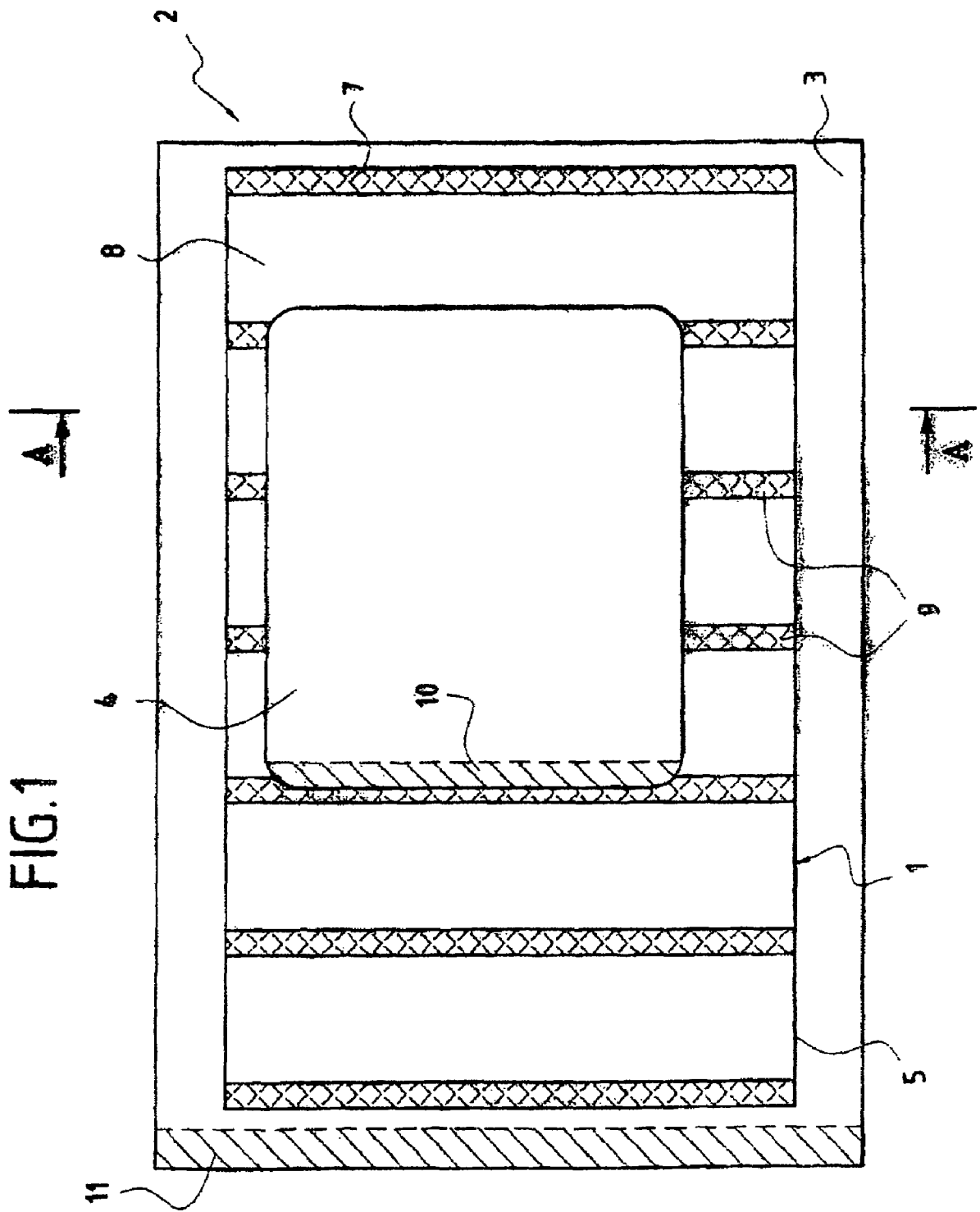
FIG. 1 depicts, in a view from above, an item according to the invention prior to the activation of the compress it contains.

The compress 1 according to the invention comes as an integral part of an item 2 as illustrated in FIG. 1.

The item 2 is made up of an outer sachet 3, which is both watertight and airtight, and constitutes an anti-germ barrier. The walls of the sachet 3 are made, for example, of a plastic constituting an anti-germ barrier, particularly a polyamide/polyethylene blend. Such material has the special feature of being compatible with a sterilization treatment using gamma-radiation. That means that, on the one hand, this material is not degraded during such a sterilization treatment and, on the other hand, that is allows the gamma-radiation to pass, thus allowing the elements contained in the outer sachet 3 to be sterilized effectively. It then keeps the elements it contains sterile.

In the preferred embodiment of the invention depicted in the figure, the walls of the sachet 3 are transparent, which means that they can be seen through. This advantageously allows the condition of the elements contained inside the sachet 3 to be checked.

Arranged inside the sachet 3 are the compress 1 and a pouch 4 full of water.

The compress 1 is produced in the form of a wrapper 5 inside which particles 6 of a polymer with a high water absorption capacity are arranged, initially in the dry state. The particles 6 are entirely nontoxic.

It is these polymer particles which form the basis of the cooling effect produced by the compress, according to a known general principle. The particles 6, when activated, that is to say when they have swollen with the water that they have absorbed, and possibly spent time in a cold place, generate cold by vaporization and desorption of the water absorbed.

Polymer particles 6 which prove to be advantageous in the context of the invention have a water absorption capacity of about 60 times their volume. These are, in particular, particles of crosslinked polyacrylate, although this embodiment does not in any way restrict the invention.

The wrapper 5 which contains the particles 6 is made of a water-permeable nonwoven material. This material is compatible with a sterilization treatment using gamma-radiation, which means on the one hand that it can withstand such a treatment and, on the other hand, that it does not block the passage of the gamma-radiation, thus allowing the particles 6 located inside the wrapper to be sterilized.

In addition, the material of which the wrapper is made has good resistance to the pressure exerted on the walls of the wrapper by the polymer particles as these swell by absorbing water, and therefore expand a great deal and rapidly.

In particular, the wrapper is made entirely of polypropylene.

The amount of particles 6 in the dry state contained within the wrapper is such that there is still a great deal of empty space within the wrapper, so as to allow the particles to expand as they absorb water. Thus, the wrapper is in a particularly flat form when the polymer particles are in the dry state, whereas is has a thickness that may be several centimeters when the particles are swollen with water.

In addition, the amount of particles 6 in the dry state contained in the wrapper 5 is greater than the amount just required to fill the wrapper completely when the particles are swollen with water. In particular, it is between 400 and 800% of this amount.

In other words, by way of example, for a wrapper with an internal volume of 100 ml, and polymer particles with a water absorption capacity of 60 times their volume, if 1.65 ml of particles were introduced into the wrapper, once they had swollen with water they would occupy a volume 60 times greater, that is to say approximately equal to 100 ml. The quantity of 1.65 ml of particles in the dry state would therefore be the amount just needed to fill the 100 ml of volume within the wrapper when the particles have completely swollen with water.

According to the invention, an amount of polymer particles 6 that is four to eight times greater, and preferably six times greater, is introduced. Thus, still in the example of a wrapper with an internal volume of 100 ml, 6 to 13 ml, preferably about 10 ml of polymer particles by mass is readily accessible, by performing a calculation that is within the competence of the person skilled in the art, from the density of the particular polymer chosen.

This makes it possible in an entirely advantageous way to ensure that, even if there is a degradation of some of the polymer particles, or partial destruction of the crosslinking, when the compress is being sterilized, there are still enough working particles to completely fill the pouch after the water has been absorbed, and to deliver an effective amount of coldness.

Along its edges, the wrapper is sealed with weld lines 7 to prevent the particles 6 from escaping therefrom.

The weld lines 7 are relatively wide, preferably between 3 and 7 mm wide, and this improves their resistance to the force exerted on them by the polymer particles 6 which expand as they absorb water. The welding technique used is preferably ultrasonic welding, in continuous lines or criss-cross lines. However, any other welding technique that gives the weld line produced good strength can also be used within the context of the invention.

The wrapper 5 of the compress is preferably produced in such a way as to form a plurality of elongated compartments 8, inside which the particles 6 are uniformly distributed. In the exemplary embodiment depicted in the figure, the wrapper forms six compartments. This shape allows the compress to have a uniform area of contact with the body on which it is to be applied, and for this to be true over the entire surface area of the compress.

Any other shape of wrapper or of the compartments also falls within the scope of the invention.

The compartments 8 are delimited from one another by weld lines 9. These weld lines are produced in a similar way to the weld lines 7 produced at the ends of the wrapper 5. As a result, the intermediate weld lines 9 have good resistance to the forces that may be exerted on them.

It is thus advantageously ensured that, even if some of the fibers of the material of which the wrapper is made are degraded during the sterilization treatment using gamma-radiation or beta-radiation, the weld lines 7 and 9 will only be weakened slightly and will remain strong enough after sterilization to maintain their integrity throughout the use of the compress.

Inside the outer sachet 3, a pouch 4 filled with water is associated with the compress 1.

The pouch 4 is made of a watertight material which is also, like the materials of which the walls of the outer sachet 3 and the wrapper 5 of the compress are made, compatible with a sterilization treatment using gamma-radiation. Thus, on the one hand, this material is not degraded by gamma-radiation and, on the other hand, it does not impede its passage, which means that the water contained inside the pouch 4 can be sterilized by such a treatment.

The walls of the pouch 4 are made in particular of a plastic. For example, they are based on polyethylene.

The pouch 4 is hermetically sealed, particularly by welding. The welds produced are strong enough not to yield when the item is handled for its transportation. However, at least one of the welds is designed such that it can yield, at least in part, under the effect of pressure exerted by the user on the exterior surface of the pouch. For example, at least one of the welds 10 is less that 0.5 mm wide, at least in one of its regions.

Thus, when it is desired for the water contained in the pouch 4 to spread out from this pouch, a fairly firm pressure exerted by had on the pouch allows the so-called frangible region 10 of the pouch to be ruptured and the water released. In all other cases, if weaker forces are accidentally exerted on the pouch, there is little or no risk of it rupturing.

The amount of water contained in the pouch 4 is approximately equal to, and preferable slightly less than, the volume remaining free in the wrapper 5 of the compress once the polymer particles 6 have been introduced thereinto. Thus, still in the example of a wrapper 5 with an internal volume of 100 ml, if this wrapper for example contains 10 ml of polymer particles 6 in the dry state, then a pouch of water containing 90 ml of water, or preferably 89 ml of water, will be associated with it. Thus, if can advantageously be guaranteed that all of the water contained in the pouch 4 will indeed be able to enter the wrapper 5, where it will be absorbed by the polymer particles.

An item according to the invention is manufactured as follows.

A compress 1 is prepared, in the form for example of a set of compartments each containing a suitable amount of polymer particles 6 in the dry state.

A pouch of water 4 is prepared independently, taking care to form on its surface, particularly at a weld line, a frangible region 10. The pouch 4 contains only the right amount of water, which is determined according, on the one hand, to the internal volume of each of the compartments 8 and, on the other hand, to the amount of polymer particles 6 contained in each of the compartments and the water absorption capacity of these particles. It is also advantageous for the pouch 4 to contain as little air as possible.

Figure 2:
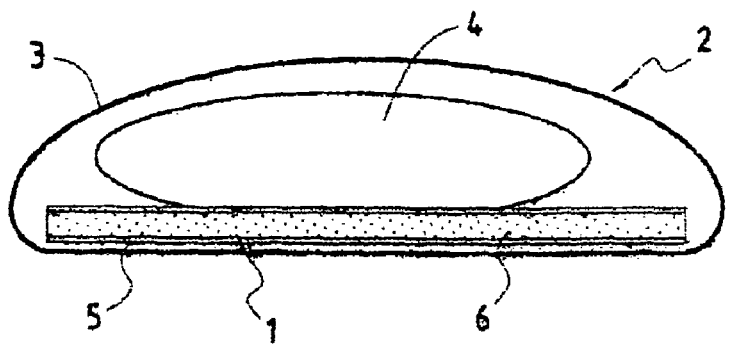
FIG. 2 illustrates the item of FIG. 1, viewed in section on A-A.

The compress 1 and the pouch 4 are then inserted into as outer sachet 3 which is voluminous enough to contain them placed flat one upon the other. This then yields the item depicted in section on A-A in FIG. 2.

A reduced pressure is then applied inside the sachet, and the latter is sealed. The sachet 3 is sealed in particular by welding. The weld line 11 produced is wide and strong so as, on the one hand, to guarantee that the sachet is both watertight and airtight and, on the other hand, to make sure that when the user presses the surface of the sachet 3 in order to rupture the inner pouch of water 4, it will indeed be the frangible region 10 of the latter which ruptures, rather than the weld line 11 sealing the sachet. This is further encouraged through the fact that a reduced pressure has been applied to the inside of the sachet, which means that the pressure exerted on the surface of the sachet 3 is transmitted directly to that of the pouch 4. As a safety measure, it is advantageous to provide a double weld for sealing the sachet 3.

Figure 3:
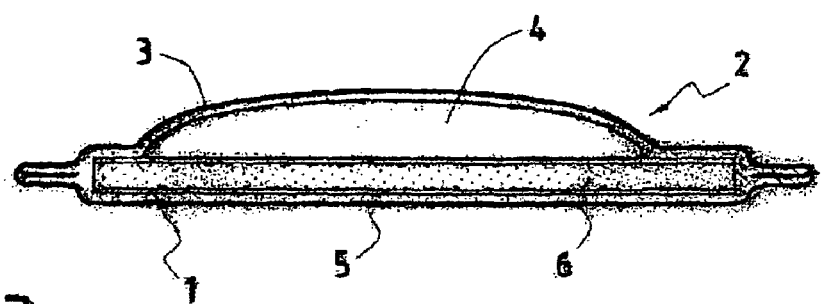
FIG. 3 shows the item of FIG. 2 in a vacuum pack.

The item is then in the configuration set out in FIG. 3. The pouch of water 4 is pressed firmly against the surface of the compress 1. The walls of the outer sachet 3 are struck against the surfaces of the compress 1 and of the pouch 4.

Once this operation has been performed, the item 2 is subjected to a sterilization treatment using gamma-radiation, or beta-radiation. The inside of the sachet 3, including the compress 1 and the water in the pouch 4, is therefore rendered sterile. None of the elements contained inside the sachet experiences damage, except for some of the particles 6 whose crosslinking is destroyed. However, enough working particles remain to be able to deliver an effective coldness.

Because of the properties of the material of which the walls of the sachet 3 are made, no contaminants can then enter the sachet. The item can thus be kept in complete safety, maintaining the sterility of the elements contained in the sachet.

When it is desired to use the compress 1 for its cooling effect, all that is required, without opening the sachet 3, is to press on the surface thereof so as to apply pressure to the wall of the pouch 4 and rupture the frangible region 10, thereby releasing the water contained in the pouch 4.

The water spreads out inside the sachet and quite naturally enters the compress 1, where it is absorbed by the polymer particles 6. The water naturally spreads out between the various compartments 8. However, a uniform and rapid distribution is encouraged when the item is held in a position such that the pouch of water is situated above the compress, and approximately centered over the latter, at the time that the pouch 4 is ruptured.

The swelling of the compartments 8 is then seen. As they expand by absorbing water the particles exert a relatively firm pressure against the walls of the wrapper 5 that contains them. The walls of the outer sachet 3, which are stuck against the surface of the compress 1, absorb some of these mechanical forces exerted on the wrapper 5, thus acting as a reinforcement thereof, and improving its ability to withstand these forces.

When the water that was contained in the pouch 4 has completely entered the compress, which in practice takes just a few minutes, the item is placed, still without opening it, in a cold place, particularly in a freezer. It is kept in this place for 15 to 90 minutes depending on the capability of the freezing apparatus used, so as to cool the water absorbed in the polymer particles and convert it into ice. This will make it possible for the compress to achieve better inertia in terms of its regaining of temperature while it is being used.

Because of the reduced pressure inside the sachet, there are only a very few traces of moisture in the air surrounding the compress. A deposit of ice through the condensation of moisture at the surface of the compress during the time it spends in the freezer therefore does not form. The surface of the compress remains dry, which will make it all the more comfortable to use. In addition, it will not wet the skin, and in particular the wound to which it is going to be applied, and this will encourage rapid healing of this wound.

Figure 4:
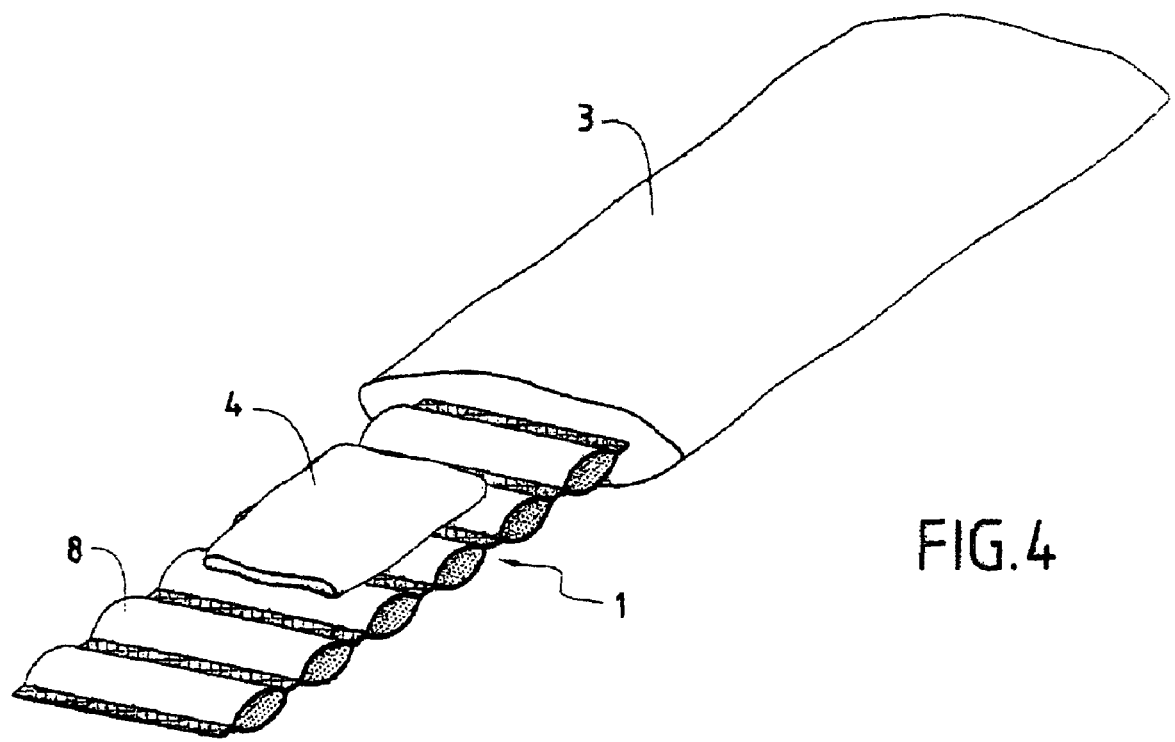
FIG. 4 depicts an overall view of an activated compress ready for use as it leaves the outer sachet.

The item 2 is tem removed from the freezer. The compress 1 present within it is activated, that is to say is producing its cooling effect. It is entirely sterile. All the user then needs to do is to open the sachet 3, respecting all the appropriate sterility conditions, and remove the compress therefrom. The compress is then in a form resembling sausages, as depicted in FIG. 4. It is ready to be applied to the body in order to supply its cooling effect thereto in complete safety.

It is particularly suited to a single use, and may be discarded after use.

By way of example, a compress according to the invention is made up of crosslinked sodium polyacrylate particles with a water absorption capacity of 60 times their volume. The compress is made up of six elongate sausages, like the one illustrated in the figures. Each compartment has an internal volume of 23 ml and contains 2.7 ml of polymer particles. The inner pouch associated with the compress contains 120 ml of water.

The compress is prepared in a sterile pack in the item according to the invention, and activated according to the procedure described hereinabove.

Having spent 90 minutes in the freezer, the compress is extracted from the outer sachet. Its exterior surface is dry, which means that it is very comfortable to use when applied to the body.

It maintains a temperature of between 3 and 12° C. for 60 minutes.

This performance is equivalent to that of compresses prepared and activated in the conventional way, which are not subjected to sterilization prior to their use.

The foregoing description clearly explains how the invention is able to achieve its set objectives. In particular, it provides a compress in a sterile pack, which allows an effective cooling action and is comfortable to use.

It is nonetheless evident from the foregoing that the invention is not restricted to the embodiments specifically described and depicted in the figures and that, on the contrary, it extends to cover any variant that employs equivalent means.

In particular, the compress described hereinabove has only a cooling action. Of course, it is possible to also incorporate into the compress an active treatment agent, of the medical or paramedical type. The active agent may in particular be initially present in solution in the water contained in the inner pouch, and in this case it enters the compress with the water. It may also be present in solid form, within the wrapper, mixed in with the polymer particles. When the compress is applied to the body, the active agent produces its effect thereon. This then advantageously yields a double effect, that of cooling and that of treating. Examples of active agents that can be used within the context of the invention, provided that they are compatible with the chosen sterilization treatment, are as follows: antiseptics, anti-inflammatories, local anesthetics, agents that reduce swelling, agents that promote healing.

The invention claimed is:

1. A sealed watertight outer sachet;
    an inner pouch filled with water within the sealed watertight outer sachet, the inner pouch comprising a wall with a frangible region;
    a compress having a cooling effect within the sealed watertight outer sachet, the compress comprising a wrapper that is at least partially water permeable, and particles of a polymer having a high water absorption capacity in a dry state enclosed within the wrapper;
    wherein:
    the compress is separate from the inner pouch;
    the sealed watertight outer sachet comprises a material that keeps the inner pouch and the compress sterile after the article is sterilized; and
    the frangible region of the inner pouch is configured to be broken by exerting pressure through the sealed watertight outer sachet on the inner pouch, thereby releasing water from the inner pouch to activate the compress, without opening the sealed watertight outer sachet.

2. The article according to claim 1, wherein said inner pouch contains a volume of water at least equal to the volume available in said wrapper to allow said particles to swell by absorbing water.

3. The article according to claim 1, wherein said inner pouch contains a volume of water less than the volume available in said wrapper to allow said particles to swell by absorbing water.

4. The article according to claim 3, wherein the particles are present in an amount of 400 to 800% by comparison with the quantity that is sufficient to fill said wrapper when said particles have swelled fully by absorbing water.

5. The article according to claim 1, wherein the particles are present in an amount of 400 to 800% by comparison with the quantity that is sufficient to fill said wrapper when said particles have swelled fully by absorbing water.

6. The article according to claim 1, wherein said polymer particles are present in an amount of about 600% by comparison with the quantity that is sufficient to fill said wrapper when said particles have swelled fully by absorbing water.

7. The article according to claim 1, wherein said particles have a water absorption capacity of about 60 times their volume, and wherein, for an internal volume of 100 ml within the wrapper, an amount of the particles in the dry state contained in said wrapper ranges from 6 to 13 ml and the inner pouch contains a volume of water equal to complement the volume of particles to make a total volume of up to 99 ml.

8. The article according to claim 7, wherein the amount of the particles in the dry state contained in said wrapper is 10 ml.

9. The article according to claim 1, wherein the sealed watertight outer sachet is airtight, and said inner pouch and said compress are vacuum packed with the sealed watertight outer sachet, an interior of the sealed watertight outer sachet being under reduced pressure.

10. The article according to claim 1, wherein opposite faces of said wrapper of the compress are connected together along various longitudinal lines so as to form a plurality of elongate compartments in which said particles are uniformly distributed.

11. The article according to claim 1, wherein said wrapper is made of a water-permeable nonwoven material.

12. The article according to claim 1, wherein said watertight sealed watertight outer sachet, said inner pouch and said compress are compatible with a sterilization treatment using gamma-radiation.

13. The article according to claim 12, wherein said sealed watertight outer sachet, said inner pouch and said compress are compatible with a sterilization treatment using gamma-radiation ranging from 20 to 50 kGy.

14. The article according to claim 1, wherein said sealed watertight outer sachet, said inner pouch and said compress are compatible with a sterilization treatment using beta-radiation.

15. A sealed article comprising:
    a sealed watertight outer sachet;
    an inner pouch filled with water centrally situated within the sealed watertight outer sachet, the inner pouch comprising a wall with a frangible region;
    a compress having a cooling effect within the sealed watertight outer sachet, the compress comprising a wrapper that is at least partially water permeable; and particles of a polymer having a high water absorption capacity in a dry state enclosed within the wrapper;
    wherein:
    the compress is separate from the inner pouch, and the inner pouch is in contact with an outer surface of the wrapper of the compress;
    the inner pouch and the compress are vacuum packed within the sealed watertight outer sachet, an interior of the sealed watertight outer sachet being under reduced pressure;
    the water from within the inner pouch activates the compress when the frangible region is broken; and
    the sealed watertight outer sachet comprises a material that keeps the inner pouch and the compress sterile after the article is sterilized.

16. A method of manufacturing a sealed article, the method comprising:
    preparing a compress having a cooling effect, the compress comprising a wrapper that is at least partially water permeable, and particles of a polymer having a high water absorption capacity in a dry state enclosed within the wrapper;
    introducing the compress and an inner pouch filled with water into an outer sachet, the inner pouch comprising a wall with a frangible region; and
    applying a reduced pressure to an inside of the outer sachet and sealing the outer sachet in a watertight manner to produce a sealed watertight outer sachet;
    wherein:
    the compress is separate from the inner pouch;
    the sealed watertight outer sachet comprises a material that keeps the inner pouch and the compress sterile after the article is sterilized; and
    the frangible region of the inner pouch is configured to be broken by exerting pressure though the sealed watertight outer sachet on the inner pouch, thereby releasing water from the inner pouch to activate the compress, without opening the sealed watertight outer sachet.

17. The method according to claim 16, further comprising sterilizing the sealed article by treating the sealed article with gamma-radiation ranging from 20 to 50 kGy, or by treating the sealed article with beta-radiation.

18. The method according to claim 16, wherein opposite faces of the wrapper of the compress are connected together along various longitudinal lines so as to form a plurality of elongate compartments in which the particles are uniformly distributed, the lines being formed by ultrasonic welding in continuous lines.

19. The method according to claim 16, wherein opposite faces of the wrapper of the compress are connected together along various longitudinal lines so as to form a plurality of elongate compartments in which the particles are uniformly distributed, the lines being formed by ultrasonic welding in criss-cross lines.

20. A method of using a sealed article, the method comprising:
  providing a sealed article that has been sterilized, comprising:
    a sealed watertight outer sachet;
    an inner pouch filled with water within the sealed watertight outer sachet, the inner pouch comprising a wall with a frangible region;
    a sterile compress having a cooling effect within the sealed watertight outer sachet, the compress comprising a wrapper that is at least partially water permeable; and particles of a polymer having a high water absorption capacity in a dry state enclosed within the wrapper;
  wherein:
    the compress is separate from the inner pouch;
    the sealed watertight outer sachet comprises a material that keeps the inner pouch and the compress sterile after the article has been sterilized; and
    the frangible region of the inner pouch is configured to be broken by exerting pressure through the sealed watertight outer sachet on the inner pouch;
  applying sufficient pressure to the inner pouch in order to break the frangible region, thereby releasing water from the inner pouch to allow the water to penetrate the compress, without opening the sealed watertight outer sachet;
  optionally placing the article in an environment below room temperature for a time ranging from 15 to 90 minutes; and
  opening the sealed watertight outer sachet and removing the sterile compress.

* * * * *